United States Patent [19]

Tsuji

[11] Patent Number: 5,208,457
[45] Date of Patent: May 4, 1993

[54] METHOD OF SECONDARY ION MASS SPECTROMETRY ANALYSIS

[75] Inventor: Tsutomu Tsuji, Tokyo, Japan
[73] Assignee: NEC Corporation, Tokyo, Japan
[21] Appl. No.: 755,779
[22] Filed: Sep. 6, 1991
[30] Foreign Application Priority Data
  Sep. 7, 1990 [JP] Japan .................................. 2-237438
[51] Int. Cl.$^5$ ............................................ G01N 23/00
[52] U.S. Cl. ..................... 250/282; 250/306; 250/309; 250/397
[58] Field of Search ............... 250/282, 281, 306, 307, 250/309, 397, 399

[56] References Cited
U.S. PATENT DOCUMENTS
  4,694,170  9/1987  Slodzian et al. ..................... 250/309
  4,740,697  4/1988  Suzuki ................................. 250/309

Primary Examiner—Jack I. Berman
Assistant Examiner—Kiet T. Nguyen
Attorney, Agent, or Firm—Burns, Doane, Swecker & Mathis

[57] ABSTRACT

A method of secondary ion mass spectrometry analysis has been improved to make detection of the positive and the negative secondary ions within a short period of time and with a high sensitivity. This improved method utilizes an accelerated primary ion of a cesium oxide for selective irradiation to a specific region in the test specimen to sputter the specimen surface and to make a mass spectrometry analysis of emitted positive and negative secondary ions. In detecting the positive and the negative secondary ions, it is possible to change the polarity of one ion current detection electrode of a secondary ion mass spectrometer in turn or to use two ion current detection electrodes connected to a secondary ion mass spectrometer and applied to a positive and a negative potential, respectively.

4 Claims, 4 Drawing Sheets

METHOD OF SECONDARY ION MASS SPECTROMETRY ANALYSIS

BACKGROUND OF THE INVENTION

1. Field of the invention

The present invention relates to a method of Secondary Ion Mass Spectrometry (SIMS) analysis, and more particularly to a method of SIMS analysis which enables high sensitivity mass spectrometry of two or more elements of different electro-negativities in the same analysis.

2. Description of the prior art

The SIMS is a method for evaluating specimen construction by obtaining a concentration distribution of an element in a direction toward the depth and/or the surface of a specimen. Such concentration distribution is obtained by irradiating a primary ion beam of $O_2^+$, $Cs^+$, $Ar^+$, $N_2^+$ or the like toward a surface of a specimen in a highly evacuated vacuum chamber to emit neutral atoms, secondary ions and secondary electrons by a sputtering phenomenon and selecting a specific secondary ion by means of a secondary ion mass spectrometer. It is possible to detect not only ratios but also concentrations of impurity elements or constitutional elements in a specimen by determining the secondary ion current intensity as the sputtering proceeds.

Up to the present, it is usual to use a specific primary ion source selected in accordance with the degree of electro-negativity of an element to be detected, in order to get high detection sensitivity by SIMS. For example, in case an element having a large electro-negativity such as sulfur (S) is detected, $Cs^+$ which is a positive ion is irradiated as a primary ion to reduce the work function of the element to be detected and to accelerate emission of the negative secondary ion $S^-$. To the contrary, in case an element having a small electro-negativity such as chromium (Cr) is detected, $O_2^+$ or $O^-$ which is a negative ion is irradiated as a primary ion to accelerate emission of the positive secondary ion $Cr^+$.

Accordingly, when concentration distributions of plural elements having much different electro-negativities should be determined, for example, as shown in the attached FIGS. 1(a) and 1(b), when concentration distributions of Cr and S in a specimen produced by forming an S-doped GaAs epitaxial layer 12 on the surface of a Cr-doped GaAs substrate 11 should be determined, it is usual to employ a method as explained below.

First, as shown in FIG. 1(a), the specimen is placed in a highly evacuated vacuum chamber 21 for a secondary ion mass spectrometer and an $O_2^+$ ion beam 1 is irradiated as a primary ion beam to sputter the surface of the specimen and detect the sputtering $Cr^+$ 5 emitted as a secondary ion, thereby carrying out a first analysis to obtain Cr concentration distribution toward the depth direction. In this step, an etching hole 13a is formed on the surface of the specimen by the irradiation of the $O_2^+$ ion beam 1.

By the irradiation of the $O_2^+$ ion beam 1 as above, it is possible to emit the sputtering $Cr^+$ 5 with high efficiency, but emission of S having a large electro-negativity as a secondary ion is low. Therefore, a second analysis is carried out, as shown in FIG. 1(b), by irradiating $Cs^+$ ion beam 2 as a primary ion beam to the surface of the specimen other than the etching hole 13a to sputter the surface of the specimen and detect the sputtering $S^-$ 6 emitted as a secondary ion, thereby to obtain S concentration distribution toward the depth direction. In this step, an etching hole 13b is formed on the surface of the specimen by the irradiation of the $Cs^+$ ion beam 2.

In the above method, positions of the etching holes 13a and 13b should naturally be differentiated and so the analysis is not carried out in the same region of a specimen. Further, the sputtering rate is different depending upon the primary ion beam source employed. It is therefore essentially necessary to determine depth of each of the etching holes 13a and 13b and on the basis thereof to make normalization of the scale in the depth direction of each of Cr concentration distribution and S concentration distribution toward the depth direction.

In order to solve the above problems, it has been proposed to alternately irradiate $O_2^+$ ion beam and $Cs^+$ ion beam or to repeat irradiation of a low energy $O_2^+$ ion beam, a high energy $N_2^+$ ion beam and a low energy $Cs^+$ ion beam in this order toward the same region of the specimen surface.

In any way, up to the present, it has been necessary to carry out the $O_2^+$ ion beam irradiation and the $Cs^+$ ion beam irradiation separately in accordance with the degree of electro-negativity of the elements to be detected in the prior art SIMS. Accordingly, it is required to use plural ion guns and so very troublesome and complicated procedures are required for the analysis.

SUMMARY OF THE INVENTION

An object of the present invention, therefore, is to present a method of SIMS analysis which enables analysis by means of a single ion gun and of the same region of a specimen by a rather simple process.

Thus the present invention provides a method of secondary ion mass spectrometry analysis comprising steps of (a) sputtering the surface of a specimen to be analyzed with the use of a cesium oxide ion as a primary ion beam source and (b) analyzing by means of a secondary ion mass spectrometer intensities of positive and negative secondary ions emitted by the sputtering.

In the secondary ion mass spectrometer, at least one secondary ion current detection electrode is provided for selectively detecting the positive and the negative secondary ions emitted by the sputtering. It is possible to make use of one ion current detection electrode in a secondary ion mass spectrometer by changing the polarity of the electrode in turn, or to make use of two ion current detection electrodes in a secondary ion mass spectrometer applied to a positive potential and a negative potential, respectively.

According to the present invention, an ion of a compound comprising two elements having much different masses such as $Cs_2^+O$, $Cs^+O$ or the like is irradiated as a primary ion beam. Then Cs with a larger mass invades into the pole surface of a specimen to form a Cs rich layer automatically and O with a smaller mass invades into a deep position from the surface of a specimen to an O rich layer automatically.

Following such invasions, sputtering occurs first from the Cs rich layer to emit a large number of negative secondary ions and then from the O rich layer to emit a large number of positive secondary ions.

It is possible to detect these positive and negative secondary ions, conduct a mass spectrometry analysis and obtain information of concentrations of predetermined elements, by a method of changing the polarity of one ion current detection electrode connected to an ion detector a secondary ion mass spectrometer in turn, or a method of using two ion current detection electrodes connected to an ion detector in a secondary ion mass spectrometer respectively applied to a positive potential and a negative potential.

If it were the case that the positive Cs and the negative O invade into the same depth of the specimen to be tested to sputter the specimen surface, the effect of Cs and the effect of O would be cancelled by each other and so the secondary ion intensity would not be increased.

In accordance with the present invention, however, the Cs rich layer and the O rich layer are automatically separated by the merit of large mass difference and so the effect of Cs and the effect of O can be retained independently of each other. Thus it is possible to sputter a large number of negative secondary ions from the Cs rich layer and a large number of positive secondary ions from the O rich layer.

For this, it becomes possible to detect, in the same analysis, positive and negative secondary ions in a highly sensitive and continuous manner.

BRIEF DESCRIPTION OF THE DRAWINGS

The present invention will be understood by referring to the following detailed description in conjunction with the accompanying drawings, wherein.

DESCRIPTION OF THE PREFERRED EMBODIMENTS

An embodiment of the present invention will now be described with reference to FIGS. 2(a) to 2(e) illustrating the analysis in the order of process steps.

Figure 1A:
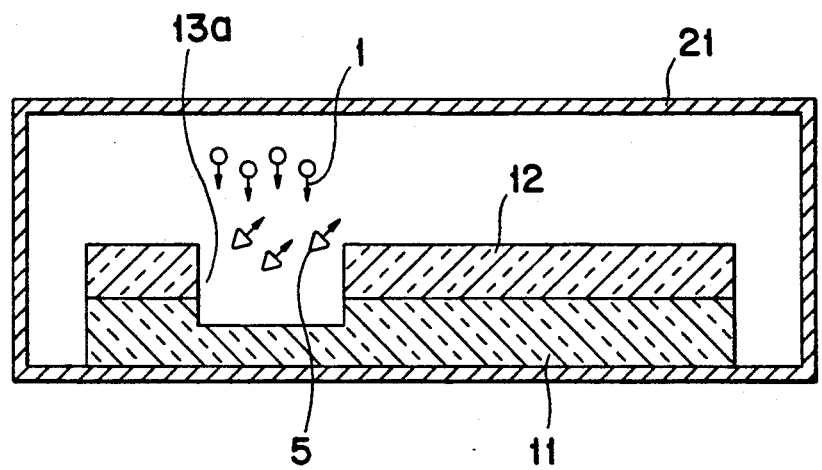
FIGS. 1(a) and 1(b) are schematic cross sectional views for illustrating a prior art secondary ion mass spectrometry analysis method.
Figure 1B:
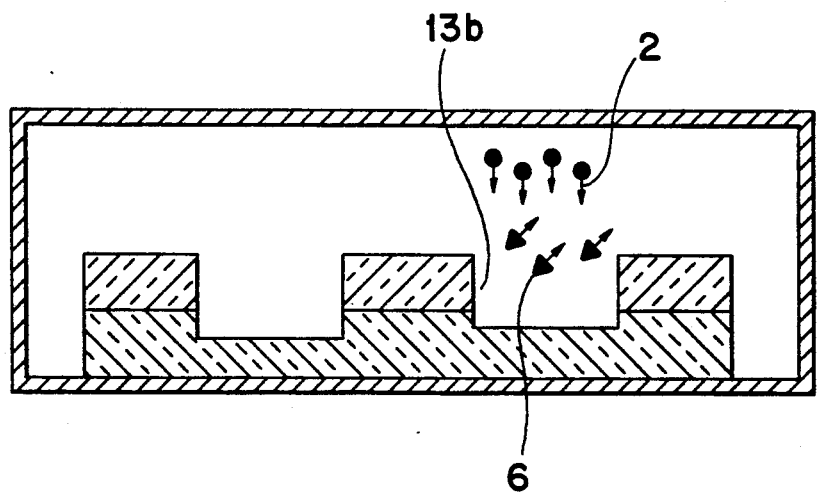
Figure 2A:
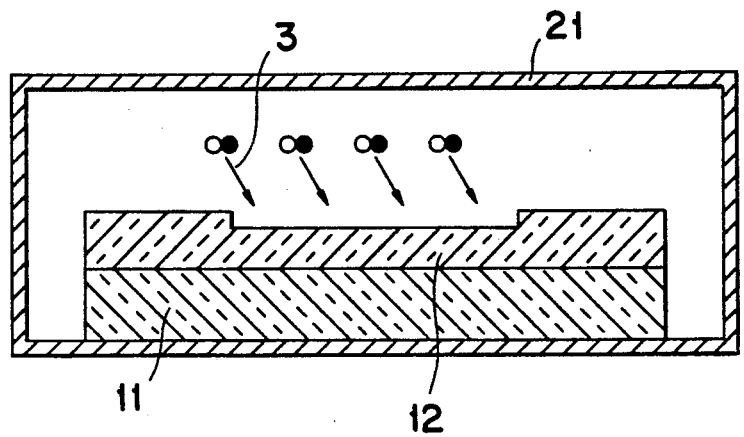
FIGS. 2(a) to 2(e) are schematic cross sectional views for illustrating an embodiment of a secondary ion mass spectrometry analysis method of the present invention.

FIG. 2(a) shows irradiation of a primary $Cs_2+O$ ion beam 3 of 3 $\mu A$ at an acceleration energy of 10 KeV selectively to a test specimen produced by forming an S-doped GaAs epitaxial layer 12 of 0.2 $\mu m$ thickness on the surface of a Cr-doped GaAs substrate 11 placed in a highly evacuated vacuum chamber 21.

Figure 2B:
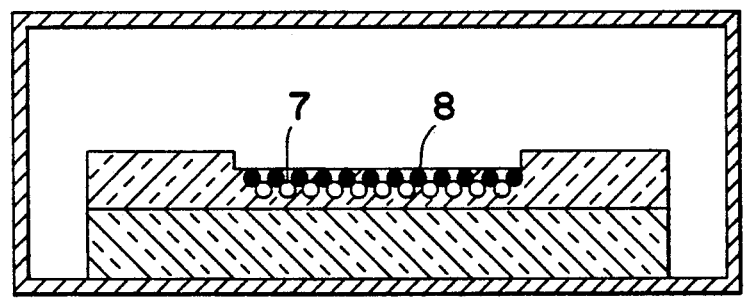

The $Cs_2+O$ ion beam 3, upon collision to the specimen surface, is decomposed into Cs 8 and Oxygen (O) 7 and as shown in FIG. 2(b), the Cs 8 of a larger mass is ion injected into the pole surface and the O 7 of a smaller mass invades into a deep region from the specimen surface.

Figure 2C:
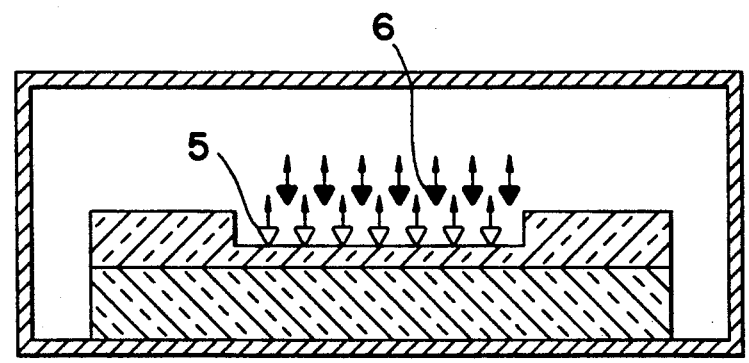

Next as shown in FIG. 2(c), GaAs in the pole surface rich in Cs 8 is sputtered and surfur (S) having a large electro-negativity and a work function reduced by Cs is emitted as a sputtering $S^-$ 6. Then GaAs in the deep region from the specimen surface rich in O 7 is sputtered and Cr having a small electro-negativity and a work function increased by O is emitted as a sputtering $Cr^+$ 5.

Figure 2D:
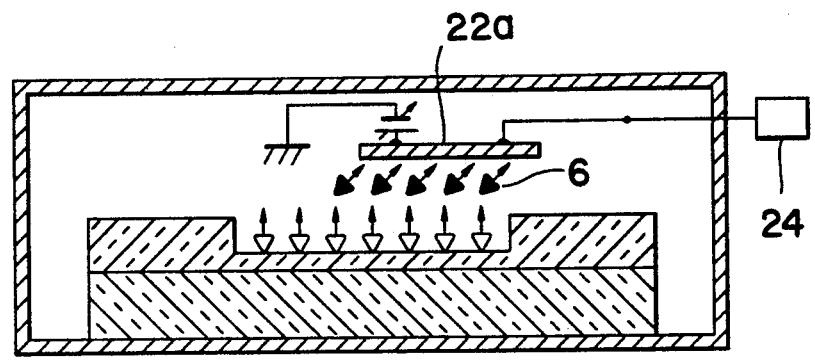

The first emitted sputtering $S^-$ 6, as shown in FIG. 2(d), enters an ion current detection electrode 22a connected to a an ion detector 24 in secondary ion mass spectrometer and applied to a positive potential.

Figure 2E:
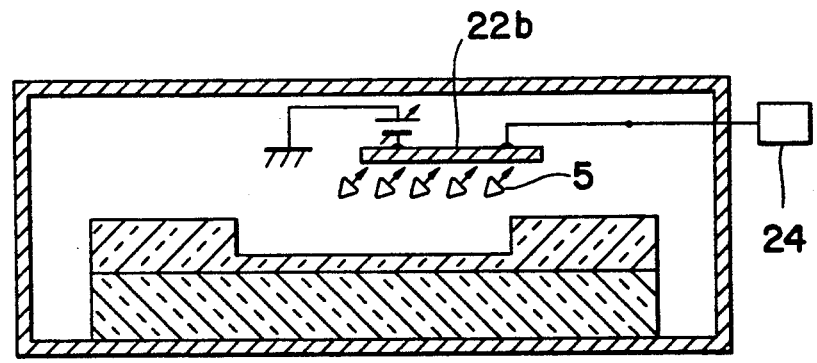

The next emitted sputtering $Cr^+$ 5, as shown in FIG. 2(e), enters an ion current detection electrode 22b connected to the ion detector 24 in the secondary ion mass spectrometer and applied to a negative potential.

In this embodiment, the negative and positive secondary ions ($S^-$ and $Cr^+$) emitted by a single time of irradiation of $Cs_2+O$ ion beam are continuously detected by changing the bias potential of the ion current detection electrode connected to the secondary ion mass spectrometer from the negative to the positive in this order, but it is also possible to detect only either one of the positive and the negative secondary ions in a single time of $Cs_2+O$ irradiation.

Another embodiment of the present invention will now be described with reference to FIGS. 3(a) to 3(d) illustrating the analysis in the order of process steps.

Figure 3A:
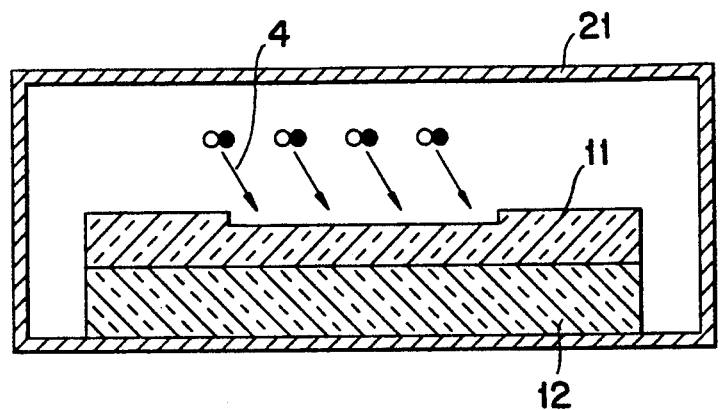
FIGS. 3(a) to 3(d) are schematic cross sectional views for illustrating another embodiment of a secondary ion mass spectrometry analysis method of the present invention.

FIG. 3(a) shows irradiation of a primary $Cs+O$ ion beam 4 of 5 $\mu A$ at an acceleration energy of 10 KeV selectively to a test specimen produced by forming an S-doped GaAs epitaxial layer 12 of 0.2 $\mu m$ thickness on the surface of a Cr-doped GaAs substrate 11 placed in a highly evacuated Vacuum chamber 21.

Figure 3B:
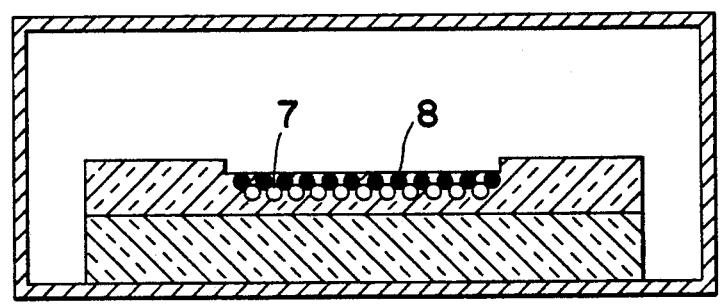

The $Cs+O$ ion beam 4, upon collision to the specimen surface, is decomposed into Cs 8 and oxygen (O) 7 and as shown in FIG. 3(b), the Cs 8 of a larger mass is ion injected into the pole surface and the O 7 of a smaller mass invades into a deep region from the specimen surface.

Figure 3C:
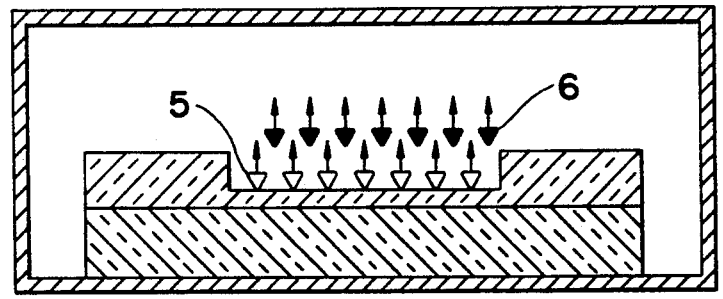

Next as shown in FIG. 3(c), GaAs in the pole surface rich in Cs 8 is sputtered and surfur (S) having a large electro-negativity and a work function reduced by Cs is emitted as a sputtering $S^-$ 6. Then GaAs in the deep region from the specimen surface rich in O 7 is sputtered and Cr having a small electro-negativity and a work function increased by O is emitted as a sputtering $Cr^+$ 5.

Figure 3D:
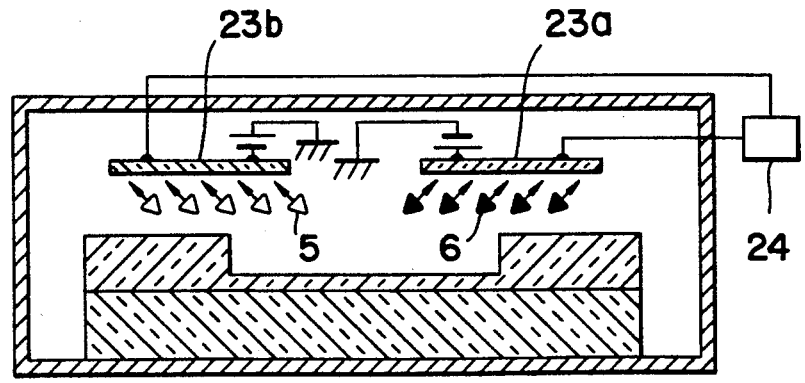

As shown in FIG. 3(d), the first emitted sputtering $S^-$ 6 enters an ion current detection electrode 23a of a positive potential connected to an ion detector 24 in a secondary ion mass spectrometer, and the next emitted sputtering $Cr^+$ 5 enters an ion current detection electrode 23b of a negative potential connected to the ion detector 24 in the secondary ion mass spectrometer.

In this embodiment, the negative and positive secondary ions ($S^-$ and $Cr^+$) can be detected for a longer time by using two ion current detection electrodes and so more highly sensitive analysis can be made when compared with the first embodiment of the present invention as explained above.

The embodiments mentioned above relate to $Cs_2+O$ and $Cs+O$ as a primary ion, but in the other cesium oxide ions, such as $Cs+O_2$ and $Cs_2+O_3$, the same results can be obtained.

As explained in detail above, the method of secondary ion mass spectrometry analysis of the present invention utilizes an accelerated primary ion of a cesium oxide for selective irradiation to a specific region in the test specimen to sputter the specimen surface and to make a secondary ion mass spectrometry analysis of emitted positive and negative secondary ions by means of at least one secondary ion current detection electrode. In detecting the positive and the negative secondary ions, it is possible to change the polarity of one ion current detection electrode in a secondary ion mass spectrometer in turn or to use two ion current detection electrodes in a secondary ion mass spectrometer and charged to a positive and a negative potential, respectively.

The present invention therefore enables detection of the positive and the negative secondary ions within a short period of time and with a high sensitivity.

I claim:

1. A method of secondary ion mass spectrometry analysis comprising steps of (a) sputtering the surface of a specimen to be analyzed with the use of a cesium oxide ion as a primary ion beam source and (b) analyzing by means of a secondary ion mass spectrometer intensities of positive and negative secondary ions emitted by the sputtering, said secondary ion mass spectrometer being provided with at least one secondary ion current detection electrode for selectively detecting the positive and the negative secondary ions emitted by the sputtering.

2. The method according to claim 1, wherein intensities of positive and negative secondary ions emitted by the sputtering are detected by changing the polarity of one ion current detection electrode in the secondary ion mass spectrometer in turn.

3. The method according to claim 1, wherein intensities of positive and negative secondary ions emitted by the sputtering are detected by using two ion current detection electrodes in the secondary ion mass spectrometer respectively applied to a positive potential and a negative potential.

4. The method according to claim 1, wherein the cesium oxide ion used is $Cs_2{}^+O$, $Cs^+O_2$, $Cs_2{}^+O_3$ or $Cs^+O$.

* * * * *